US006214874B1

(12) United States Patent
Huang et al.

(10) Patent No.: US 6,214,874 B1
(45) Date of Patent: Apr. 10, 2001

(54) TREATMENT OF HPV INDUCED CANCER USING IN SITU APPLICATION OF TWO NORDIHYDROGUIARETIC ACID DERIVATIVES, TETRAMETHYL NDGA $M_4N$ AND TETRAGLYCINAL NDGA $G_4N$

(75) Inventors: Ru Chih C. Huang, Baltimore; Jonathan D. Heller, Dundalk, both of MD (US)

(73) Assignee: John Hopkins University, Baltimore, MD (US)

( * ) Notice: Subject to any disclaimer, the term of this patent is extended or adjusted under 35 U.S.C. 154(b) by 0 days.

(21) Appl. No.: 09/418,594

(22) Filed: Oct. 15, 1999

(51) Int. Cl.$^7$ .................................................. A61K 31/22

(52) U.S. Cl. .......................... 514/551; 514/721; 560/174

(58) Field of Search .................................. 514/721, 551; 560/174; 524/721, 55

(56) References Cited

U.S. PATENT DOCUMENTS

| | | | | |
|---|---|---|---|---|
| 4,425,327 | * | 1/1984 | Moller et al. ........................... | 424/65 |
| 4,880,637 | * | 11/1989 | Jordan .................................... | 424/641 |
| 5,008,294 | * | 4/1991 | Jordan et al. ........................... | 514/731 |
| 5,559,149 | * | 9/1996 | Clum et al. ............................. | 514/529 |
| 5,827,898 | * | 10/1998 | Khandwala et al. .................. | 514/734 |
| 5,965,616 | * | 10/1999 | Wang et al. ............................ | 514/557 |

OTHER PUBLICATIONS

Chen et al., Antiviral Activities of Methylated Nordihydroguaiaretic Acids. 2. Targeting Herpes Simplex Virus Replicaton by the Mutation Insensitive Transcription Inhibitor Tetra–0 –methyl–NDGA, Journal of Medicinal Chemistry, 1998, vol. 41, No. 16, pp. 3001–3007.

Giza et al., A self–inducing runaway–replication plasmid expression system utilizing the Rop protein, Elsevier Science Publishers B.V. (Biomedical Division), 1989, pp. 73–84.

Staal et al., Antioxidants Inhibit Stimulation of HIV Transcription, Aids Research and Human Retroviruses, 1993, vol. 9, No. 4, pp. 299–306.

Gnabre et al., Isolation of anti–HIV–1 lignans from *Larrea tridentata* ounter–current Chromatography, Journal of Chromatography A., 719, 1996, pp. 353–364.

Gnabre et al., Characterization of Anti–HIV Lignans from *Larrea tridentata*, Tetrahedrom, 1995, vol. 51, No. 45, pp. 12203–12210.

Weislow et al., New Soluble–Formazan Assay for HIV–1 Cytopathic Effects: Application to High–Flux Screening of Synthetic and Natural Products for AIDS–Antiviral Activity, Journal of the National Cancer Institute, 1989, vol. 81, No. 8, pp. 577–586.

Gnabre et al., Inhibition of human immunodeficiency virus type 1 transcription and replication by DNA sequence–selective plant lignans, Proc. Natl. Acad. Sci. USA, 1995, vol. 92, pp. 11239–11243.

Gisvold et al., Lignans from *Larrea divaricata*, Journal of Pharmaceutical Sciences, 1974, vol. 63, No. 12, pp. 1905–1907.

Perry et al., Synthesis of Lignans. I. Nordihydroguaiaretic Acid[1], J. Org. Chem., 1972, vol. 37, No. 26, pp. 4371–4376.

* cited by examiner

*Primary Examiner*—James H. Reamer
(74) *Attorney, Agent, or Firm*—Pillsbury Madison & Sutro LLP (57) ABSTRACT

A method for using nordihydroguiaretic acid derivatives, in particular tetramethyl nordihydroguiaretic acid and tetraglycinal nordihydroguiaretic acid, for the localized treatment of tumors induced by human papillomavirus.

15 Claims, 8 Drawing Sheets

(3 of 8 Drawing Sheet(s) Filed in Color)

*meso*-1,4-Bis(3,4-dimethoxyphenyl)-(2*R*,3*S*)-dimethylbutane

*meso* - 1,4 - Bis [3,4 - (dimethylaminoacetoxy)phenyl]- (2*R*,3*S*)- dimethylbutane Hydrochloride Salt

C3 DMSO

TREATMENT OF HPV INDUCED CANCER USING IN SITU APPLICATION OF TWO NORDIHYDROGUIARETIC ACID DERIVATIVES, TETRAMETHYL NDGA M₄N AND TETRAGLYCINAL NDGA G₄N

The invention described and claimed herein was made in part under a grant from the National Institutes of Health. The U.S. Government has certain rights in the invention.

BACKGROUND OF THE INVENTION

1. Field of the Invention

The invention relates to the use of nordihydroguiaretic acid derivatives, in particular tetramethyl nordihydroguiaretic acid and tetraglycinal nordihydroguiaretic acid, for the treatment of tumors induced by human papillomavirus.

2. Background Information

Human papillomavirus (HPV) infection causes unregulated cell growth in many types of squamous epithelial cells, resulting in afflictions ranging from benign pallilomae (warts) to cervical, penile and mouth cancer. The strong association of these cancers with HPV and the widespread occurrence of infection denotes the importance of developing an anti HPV therapy.

Most, if not all, viruses, including those replicatively active mutants, are host dependent. They require the participation of certain cellular factors for supporting viral growth. Host cellular factors, unlike viral proteins, are not under mutational pressure and are in general, structurally invariable. Thus, compounds that block the usage of these cellular factors at different stages of the viral life cycle are likely to be good candidates as mutation insensitive antiviral drugs. Several studies using cellular factors as alternative targets for the inhibition of HIV-1 have been reviewed (1).

Applicants reported earlier that 3'-0-methylated NDGA (i.e. Mal.4), isolated from Creosote bush (Larrea tridentata) can specifically block basal HIV transcription, Tat-regulated transactivation, and HIV replication in human cell culture (2,3,4). Mal.4 exerts its effects by interfering with the binding of transcription factor Sp1 to the promoter of the HIV proviral template. The target of Mal.4 is mapped to nucleotides −87 to −40, the Sp1 binding sites of the HIV long terminal repeat (LTR). The unmodified NDGA, in vitro, does not inhibit HIV transcription and has no effect on Sp1 binding (2).

Isolation and purification of plant lignans, however, is labor intensive and costly. In anticipation of the possible clinical use of plant lignans in controlling Sp1-regulated viral and tumor growth in humans, nine different methylated NDGA activities were synthesized chemically using unmethylated NDGA as the parent substrate in large quantities with low cost (5). At drug concentrations below 30 $\mu$M, tetramethyl NDGA was found to be most effective in the control of replication HIV via inhibition of Sp1 regulated proviral transcription and transactivation (5). This study has since been extended to the control of the growth of Herpes simplex virus (HSV-1 and HSV-2) (6). Herpes simplex immediate early (IE) ICP4 gene is essential for HSV replication (7). Its promoter region possesses eight Sp1 consensus binding sites (8), five of which are required for ICP4 gene expression. It thus makes the ICP4 gene a good candidate for such testing. Applicants have found that both 3-0-methyl NDGA (Mal. 4) and tetramethyl NDGA (M₄N) are effective transcriptional inhibitors for HSV ICP4 gene expression in Vero cells via the blocking of Sp1 protein binding to the ICP4 promoter as shown by the electrophoretic mobility shift assay (6).

When the anti-HSV activities of M₄N and Mal. 4 were tested and compared to that of acycloguanosine (acyclovir, ACV) in infected Vero cells, Applicants observed that the $IC_{50}$ for M₄N varied between 11.7 $\mu$M to 4 $\mu$M for 10 passages of HSV-1 and 4 passages of HSV-2 without obvious uprising trend for requirement of higher drug concentration. However, the $IC_{50}$ for ACV increased from 7 $\mu$M for the first viral passage to 444 $\mu$M for the tenth passage of HSV-1 and to >88 $\mu$M for the fourth passage of HSV-2 indicating their rapid build-up of drug resistance against ACV in Vero cells. Consequently, while the selective index, S.I. ($TC_{50}/IC_{50}$) remained relatively stable for M₄N, the S.I. for ACV dropped 60 fold following the viral passages in Vero cells (6). Thus M₄N is a mutation insensitive drug. It can inhibit ACV resistant HSV effectively (6).

Figure 5:
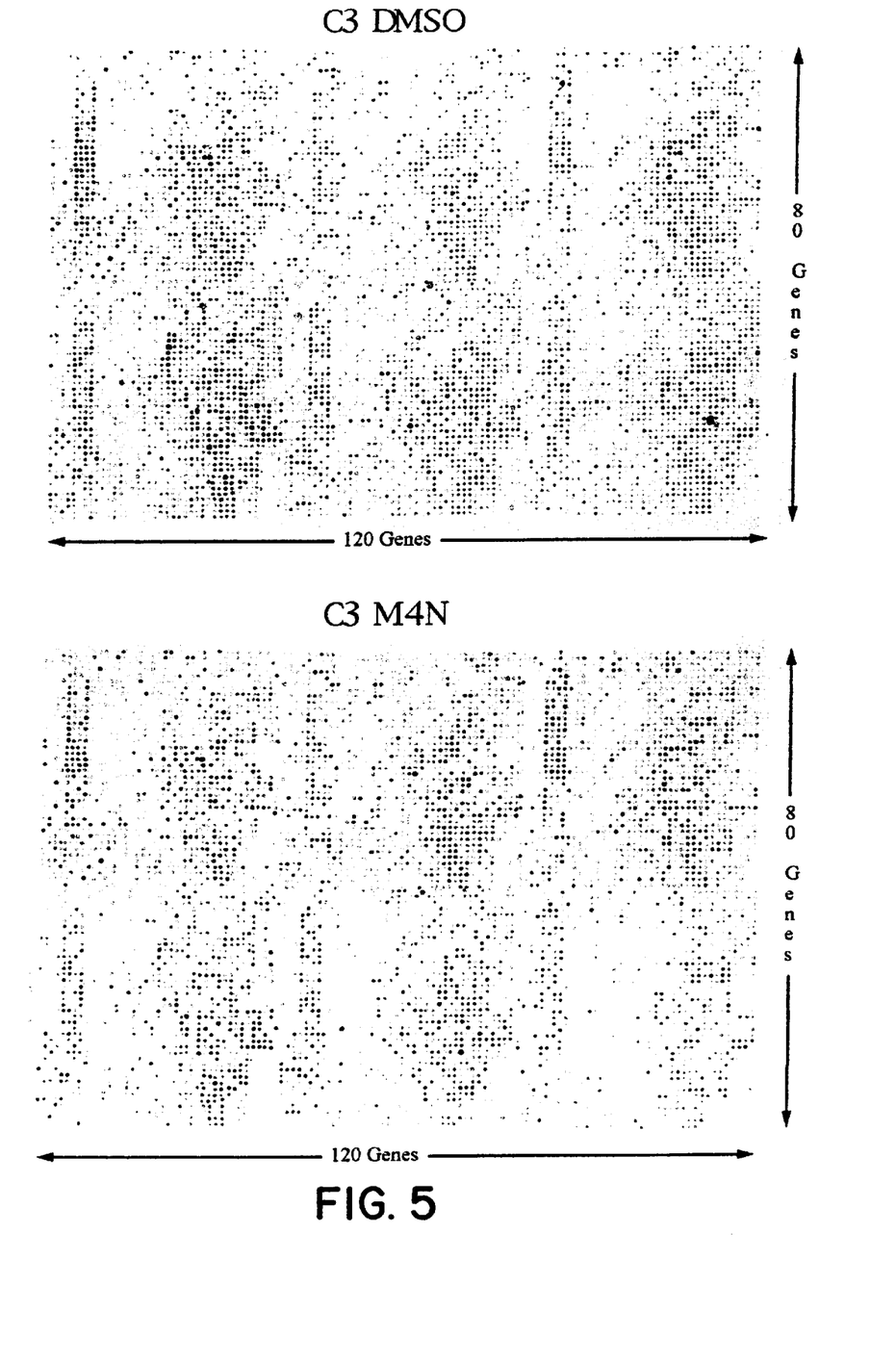
FIGS. 5A–5B. Effect of $M_4N$ on gene expression in C3 cells as examined by the GENE Assay analysis. 5A. GENE expressed in C3 cells after >2 hours of DMSA treatment (C3 DMSO). 5B. GENE expressed in C3 cells after >2 hours of $M_4N$ treatment using DMSO as solvent (C3 $M_4N$).

Due to the fact that Sp1 is an important cellular transcription factor (9), the possible inhibitory effect of this class of compounds on the expression of Sp1-regulated cellular genes should be addressed. Mal.4 cannot displace Sp1 once it is stably bound to its enhancer sites (2). It therefore seemed likely that NDGA derivatives would have a greater effect on Sp1-regulated genes in proliferating cells than on the expression of Sp1-regulated housekeeping genes in stationary cells. In the former case, the drug will be able to compete with Sp1 protein for the Sp1 sites in gene promoters during DNA synthesis, while in the latter case, the drug may have little effect on the transcribing chromatin of housekeeping genes with Sp1 protein already stably bound at their promoters. This in fact has been shown to be the case. As will be demonstrated below, by using gene array studies with 9600 expressed genes, Applicants found products of most Sp1 regulated genes remained at similar levels, are not affected by the drug treatment of cervical cancer cells C3 in culture (FIG. 5). Even so, the relatively low selective index of M₄N certainly limits its use to the lowest effective concentration if the drug must be used systemically. On the other hand, human papilloma virus induces solid cervical and oral tumors initially through the Sp1 regulated expression of HPV $E_6/E_7$ genes (10). Applicants reasoned that if drug can be delivered in situ, and be kept only in the tumor area, the drugs of high concentration may be used to effectively destroy the tumor with little damage to the patients.

SUMMARY OF THE INVENTION

It is an object of the present invention to provide a method for the treatment of tumors induced by human papillomavirus. The method comprises local application of nordihydroguiaretic acid derivatives, in particular tetramethyl nordihydroguiaretic acid (M₄N) and tetraglycinal nordihydroguiaretic acid (G₄N), to HPV-induced tumors.

Figure 1:
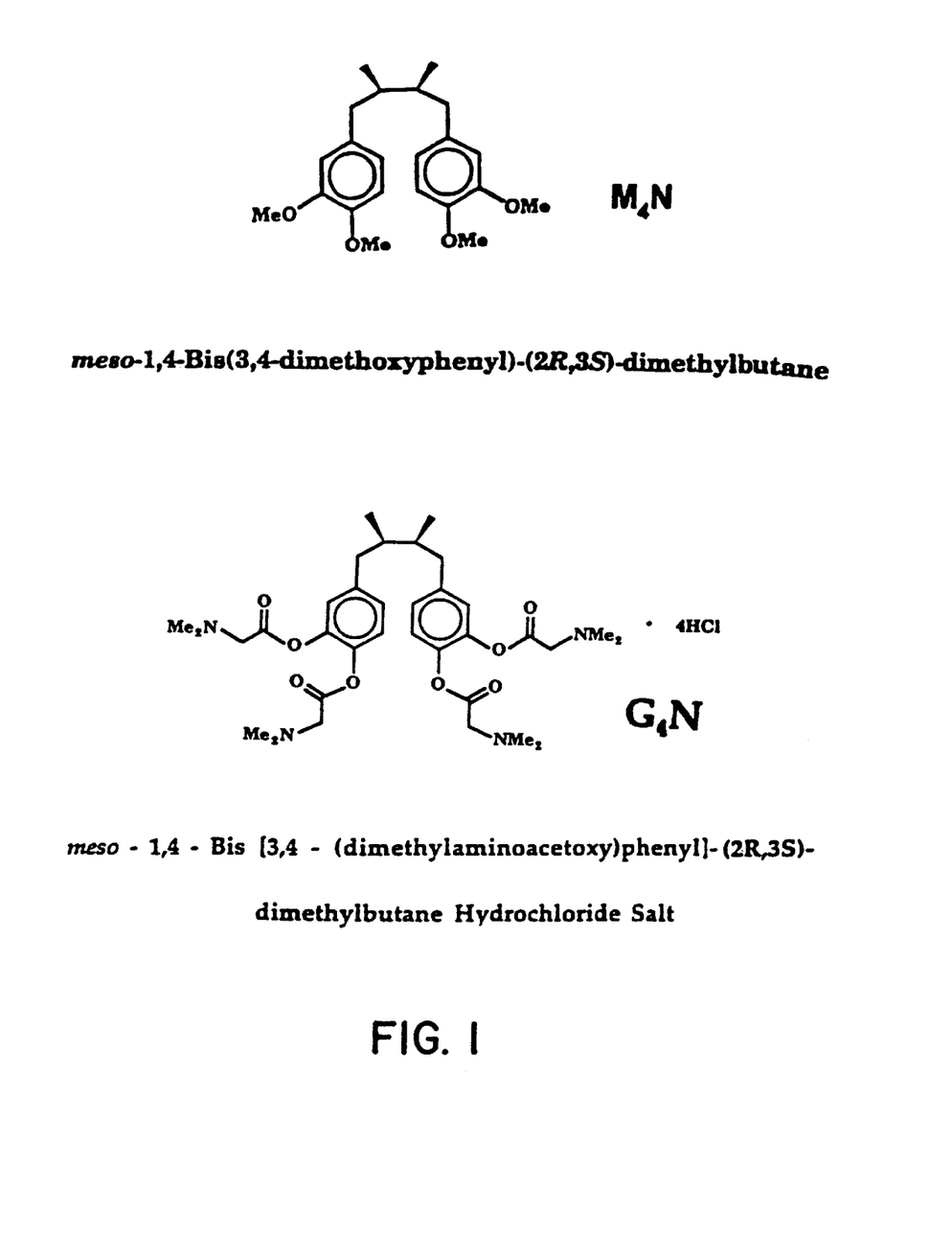
FIG. 1. Structures of $M_4N$ and $G_4N$

By nordihydroguiaretic acid derivatives is meant compounds of the structure wherein $R_1$, $R_2$, $R_3$ and $R_4$ independently represent —OH, —OCH₃, —O(C=O)CH₃, or an amino acid residue, but are not each —OH simultaneously. Particularly preferred compounds for use according to the invention are M₄N and G₄N, which are shown in FIG. 1.

HPV-induced tumors include in particular, but are not limited to, cervical, oral, penile and head and neck cancers which are associated with HPV infection.

It is contemplated that $M_4N$ and other derivatives will be administered by local injection into the tumors, generally along with pharmaceutically acceptable diluents, excipients and carriers. In preferred embodiments, $M_4N$ is injected into tumors in the form of a DMSO solution, and $G_4N$ is administered in PBS solution. The use of $G_4N$ will complement the use of $M_4N$, particularly in larger tumors (>2 cm$^3$), due to its water solubility, which allows it to spread to a larger region of the tumor. Other water-soluble and water-insoluble nordihydroguiaretic acid derivatives can be similarly employed, according to the invention.

By pharmaceutically acceptable diluents, excipients and carriers is meant such compounds as will be known to persons of skill in the art as being compatible with $M_4N$, $G_4N$ and other similar derivatives and suitable for local administration to a human or other mammal according to the invention. Although the examples hereinbelow describe administration by means of local injection, other means of local administration, such as topical application or targeted delivery to the tumor site, may also be used.

The amount of compound administered to obtain the desired treatment effect will vary but can be readily determined by persons of skill in the art. The amount of dosage, frequency of administration, and length of treatment are dependent on the circumstances, primarily on the size and type of tumor. However, dosages of from 10 mg to 20 mg of either $M_4N$ alone or with similar amounts of $G_4N$ per gram tumor weight at intervals from daily to weekly or less frequently may be mentioned for purposes of illustration. Administration of 50 μl to 100 μl of $M_4N$ dissolved in DMSO at a concentration of 200 mg/ml, either alone or in combination with $G_4N$, is expected to be effective in many cases for tumors of 1–1.5 cm$^3$.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

FIGS. 3A–3C. Inhibition of Viral $E_6$ and $E_7$ RNA Transcripts by 40 μM $M_4N$. Total RNA isolated from C3 cells treated with either 40 μM $M_4N$ or DMSO alone in growth media for 71 hours was subjected to relative RTPCR. The RTPCR samples were removed after increasing cycles of amplification and resolved on an agarose gel. The gel photographs (3A and 3B) indicate these cycles, the presence of (+) or absence (−) of $M_4N$ in the growth media, and two digests of a pGMT vector used as size markers. The amplification map (2C) indicates the two expected size products of the amplification, resulting from the alternate splicing of the early viral RNA transcript.

First column from the panel presnts the large size of tumors from mouse #4, 10, 12, following DMSO treatment (CON) as compared to the relatively small drug treated ($M_4N$ or $M_4N/G_4N$) lesions from mouse #12, 10, 27 and 20($M_4N$). The subsequent photographs are examples of these tumors examined at 100× magnification (A, B, C, DMSO treated, D untreated, E, F, G, H, $M_4N$ or $M_4N/G_4N$ treated) mice (Table 1 and Table 2).

DETAILED DESCRIPTION OF THE INVENTION

Experimental Methods

NDGA derivatives were sythesized chemically (5). Cell line C3 is a HPV16E+L plus activated Ras transformed cell line of C57 BL/6kh origin provided by W. Martin Kast of Loyola University Medical Center, Chicago, Ill., U.S.A. It is maintained and cultivated as described by Greenstone et al (11) and Feltkamp et al. (12,13).

Synthesis of $G_4N$

Standard Procedure for the Preparation of meso-1,4-Bis [3,4-(dimethylaminoacetoxy)phenyl]-(2R,3S)-dimethylbutane Hydrochloride Salt Tetraglycinyl NDGA, $G_4N$. To a dichloromethane (250 ml) solution containing NDGA (12.8 g, 42.3 mmol, 1.0 equiv) and N,N,-dimethylglycine (26.2 g, 254 mmol, 6.0 equiv) were added DCC (52.4 g, 254 mmol, 6.0 equiv) and DMAP (2.32 g, 18.9 mmol, 1.0 equiv). The reaction mixture was stirred for 24 h under nitrogen at room temperature. After the reaction mixture was filtered, the solution was concentrated under reduced pressure. Acetone (250 ml) was then added into the reaction flask and the solution was bubbled with excess HCL(g). The water-soluble precipitate was dissolved in $H_2O$ and re-precipitate twice at room temperature from acetone to give (1) (29, 2 g, 36.8 mmol) as a white solid in 87% yield. Proton NMR spectra were obtained on a Varian Unity-400 (400 MHz) spectrometer by use of $D_2O$ solvent and TSP as internal standard. Carbon-13 NMR spectra were obtained on a Varian Unity-400 (400 Mhz) spectometer by used of $D_2O$ as solvent. Carbon-13 chemical shifts are referenced to the TSP singlet (δ0.0 ppm).

The synthesis is depicted in Scheme 1.

Scheme 1

General Procedure. All reactions were carried out in oven-dried glassware (120° C.) under an atmosphere of nitrogen, unless as indicated otherwise. Acetone, dichloromethane, 1,4-dioxane, ethyl acetate, hexanes, and tetrahydrofuran were purchased from Mallinckrodt Chemical Co. Acetone was dried with 4A molecular sieves and distilled. Dichloromethane, ethyl acetate, and hexanes were dried and distilled from $CaH_2$. 1,4-Dioxane and tetrahydrofuran were dried by distillation from sodium and benzophenone under an atmosphere of nitrogen. Nordihydroguaiaretic acid was purchased from Fluka Chemical Co. N,N'-Dicyclohexylcarbodiimide (DCC), 4-dimethylaminopyridine (DMAP), morpholine, triethylamine, and potassium carbonate were purchased from Merck Inc. 1Bromo-3-chloropropane, N,N-dimethylglycine, and methyl phosphorodichloridate were purchased from Aldrich Chemical Co.

Analytical thin layer chromatography (TLC) was performed on precoated plates (silica gel 60 F-254), purchased from Merck Inc. Gas chromatographic analyses were performed on a Hewlett-Packard 5890 Series II instrument equipped with a 25-m cross-linked methyl silicone gum capillary column (0.32 mm i.d.). Nitrogen gas was used as a carrier gas and the flow rate was kept constant at 14.0 mL/min. The retention time tR was measured under the following conditions: injector temperature 260° C., isothermal column temperature 280° C. Gas chromatography and low resolution mass spectral analyses were performed on a Hewlett-Packard 5890 Series II instrument equipped with a Hewlett-Packard 5971A Mass Selective Detector and a capillary HP-1 column. Separations by medium-pressure liquid chromatography (MPLC) were performed at a flow rate of 120 mL/h by use of a Jasco Model 880-PU intelligent HPLC pump. The MPLC packing material, Reversed Phase Silica Gel C18 (particle size 0.035–0.070 mm), was purchased from Knauer Co. Purification by gravity column chromatography was carried out by use of Merek Reagents Silica Gel 60 (particle size 0.063–0.200 mm, 70–230 mesh ASTM).

Infrared (JR) spectra were measured on a Bomem Michelson Series FT-IR spectrometer. The wave numbers reported are referenced to the polystyrene 1601 cm~1 absorption. Absorption intensities are recorded by the following abbreviations: s, strong; m, medium; w, weak. Proton NMR spectra were obtained on a Varian Unity-400 (400 MHz) spectrometer by use of D2O as solvent and 3-(trimethylsilyl)propionic acid, sodium salt as internal standard. Carbon-13 NMR spectra were obtained on a Varian Unity-400 (100 MHz) spectrometer by used of D2O as solvent. Carbon-13 chemical shifts are referenced to the center of the 3-(trimethylsilyl)propionic acid, sodium salt singlet (6 0.0 ppm). Multiplicities are recorded by the following abbreviations: s, singlet; d, doublet; t, triplet; q, quartet; m, multiplet; J. coupling constant (hertz). High-resolution mass spectra were obtained by means of a JEOL JMS-HX110 mass spectrometer. meso~1,4Bis[3,4 (dimethyleminoacetoxy)phenyl]-2,3-dilnethylbutane Hydrochloride Salt (2). To a solution of NDGA (1, 12.81 g, 42.37 mmol, 1.0 equiv) and N,N-dimethylglycine (26.21 g, 254.2 mmol, 6.0 equiv) in dichloromethane (250 mL) was added DCC (52.45 g, 254.2 mmol, 6.0 equiv) and DMAP (5.176 g, 42.37 mmol, 1.0 equiv). The reaction mixture was stirred for 24 h under nitrogen at room temperature. After dicyclohexylurea in the reaction mixture was filtered off, the resultant solution was concentrated under reduced pressure. Acetone (250 mL) was then added into the residue and the resultant solution was bubbled with excess HCl (g). The precipitate was dissolved in water and re-precipitated twice by use of acetone at room temperature to give 2 (28.97 g, 36.86 mmol) as a white solid in 87% yield: 1H NMR (D2O, 400 MHz) o 0.78 (d, J=6.0 Hz, 6 H. 2×CH3), 1.73 (m, 2 H. 2×CH), 2.38 (dd, J=13.2, 9.6 Hz, 2 H. 2×ArCH), 2.78 (dd, J=13.2, 4.4 Hz, 2 H. 2×ArCH), 3.03 (s, 24 H. 8×CH3N), 4.53 (s, 8 H. 4×CH2N), 7.22 (m, 4 H. 4×ArH), 7.29 (d, J=8.4 Hz, 2 H. 2×ArH); 13C NMR(D2O, 100 MHz) 0 18.11, 40.82, 41.73, 46.75, 59.59, 125.79, 126.58, 131.63, 140.66, 142.47, 146.11, 167.84; IR (KBr) 3461 (br), 2963 (m), 1777 (s, C=O), 1620 (m), 1478 (m), 1377 (m), 1210 (m), 1106 (m), 961 (w), 852 (w) cm-l; MS (FAB) of (2–4 HCl) m/z (relative intensity) 643 (M+, 30), 600 (20),558 (43),515 (20), 473 (42), 430 (13), 388 (26), 185 (18), 93 (38),58 (100), 44 (22); HRMS (FAB) of (2–4 HCl) calcd for C34HsoN4Og 642.3628, found 642.3614; Anal. Calcd for C34Hs4N4OgCl4: C, 51.78; H. 6.90; N. 7.10; O. 16.23. Found: C, 51.70; H. 6.85; N. 7.05; O. 16.21.

EXAMPLE 1

Effect of $M_4N$ and Several Other NDGA Derivatives of SP1-regulated HPV $E_6/E_7$ Promoter Activity The effect of $M_4N$ and several other NDGA derivatives of SP1-regulated HPV $E_6/E_7$ promoter activity was examined using luciferase as a reporter. The assay depends upon DNA transfection of the HPV16 LCR ($P_{97}$ promoter) fused to the luciferase reporter gene into C33A cells by calcium phosphate methods. C33A is a cervical tumor cell line (ATCC accession no. HTB-31) that does not contain any integrated HPV DNA, but has transcription factors necessary for a robust expression of the HPV early gene promoter. One day following DNA transfection various drug concentrations dissolved with the help of dimethyl sulfoxide (DMSO) were added to the cells. Thirty hours after drug treatment (so that the assay is complete within the standard forty-eight hours for transient transfection experiments), the cells were lysed and specific luciferase activity was determined (Luciferase Assay Systems, Promega, U.S. Pat. No. 5,283,179). As the $M_4N$ drug concentration was increased the specific luciferase activity decreased.

Figure 2:
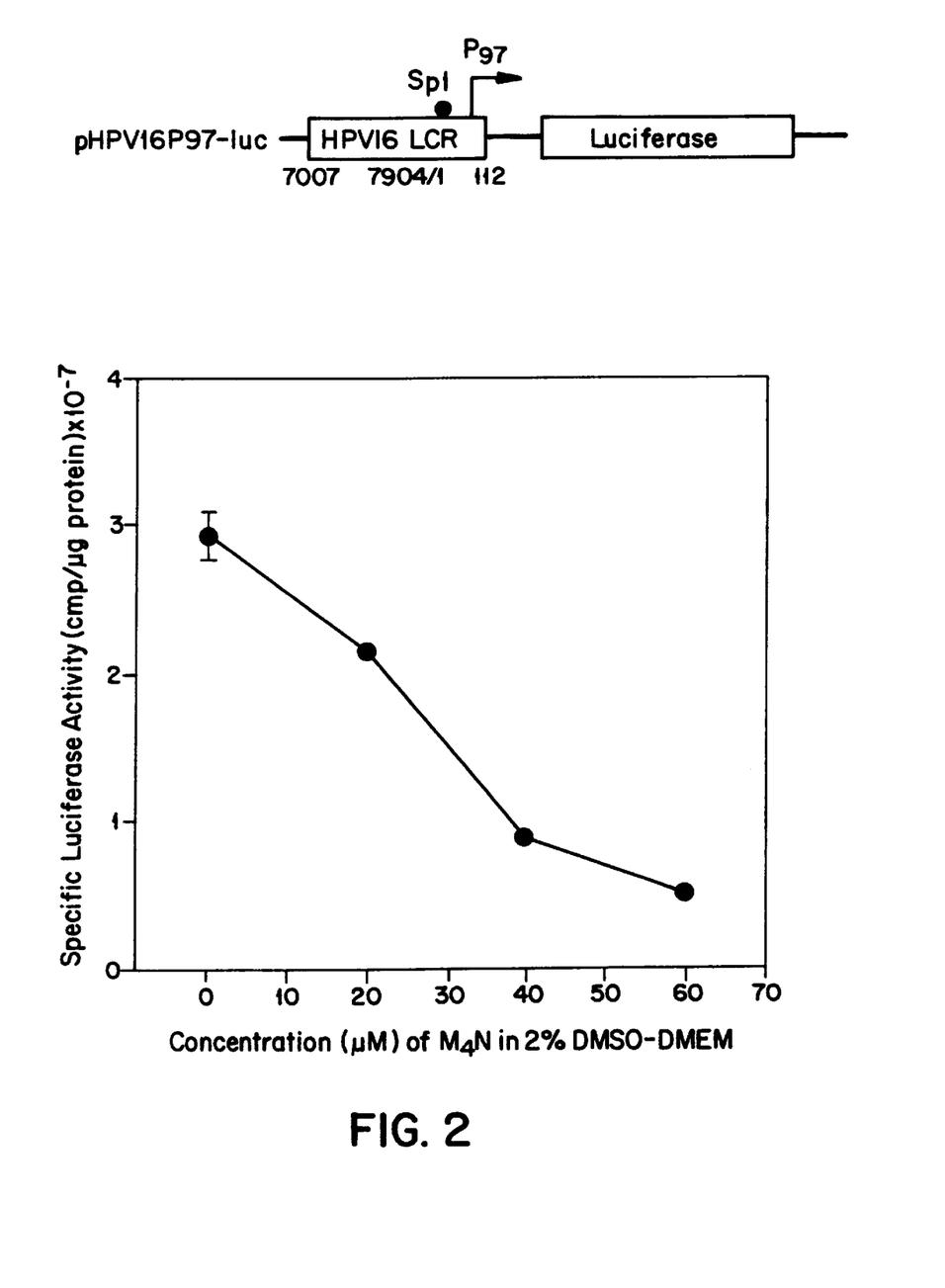
FIG. 2A. HPV-16 LCR showing region of $E_6/E_7$ promoter (pPV16P97) and the binding site for Sp1 protein.
FIG. 2B. The effect of $M_4N$ on the $E_6/E_7$ promoter activity in C-33A cells. (Inhibition of $E_6/E_7$ promoter driven luciferase gene transcription by different concentration of $M_4N$)

The results (shown in FIG. 2) demonstrate that $M_4N$ dramatically reduces Sp1 regulated transcription initiation at the HPV $E_6/E_7$ promoter in luciferase assay.

EXAMPLE 2

Inhibition of $E_6/E_7$ mRNA Synthesis Following $M_4N$ Treatment

Figure 3:
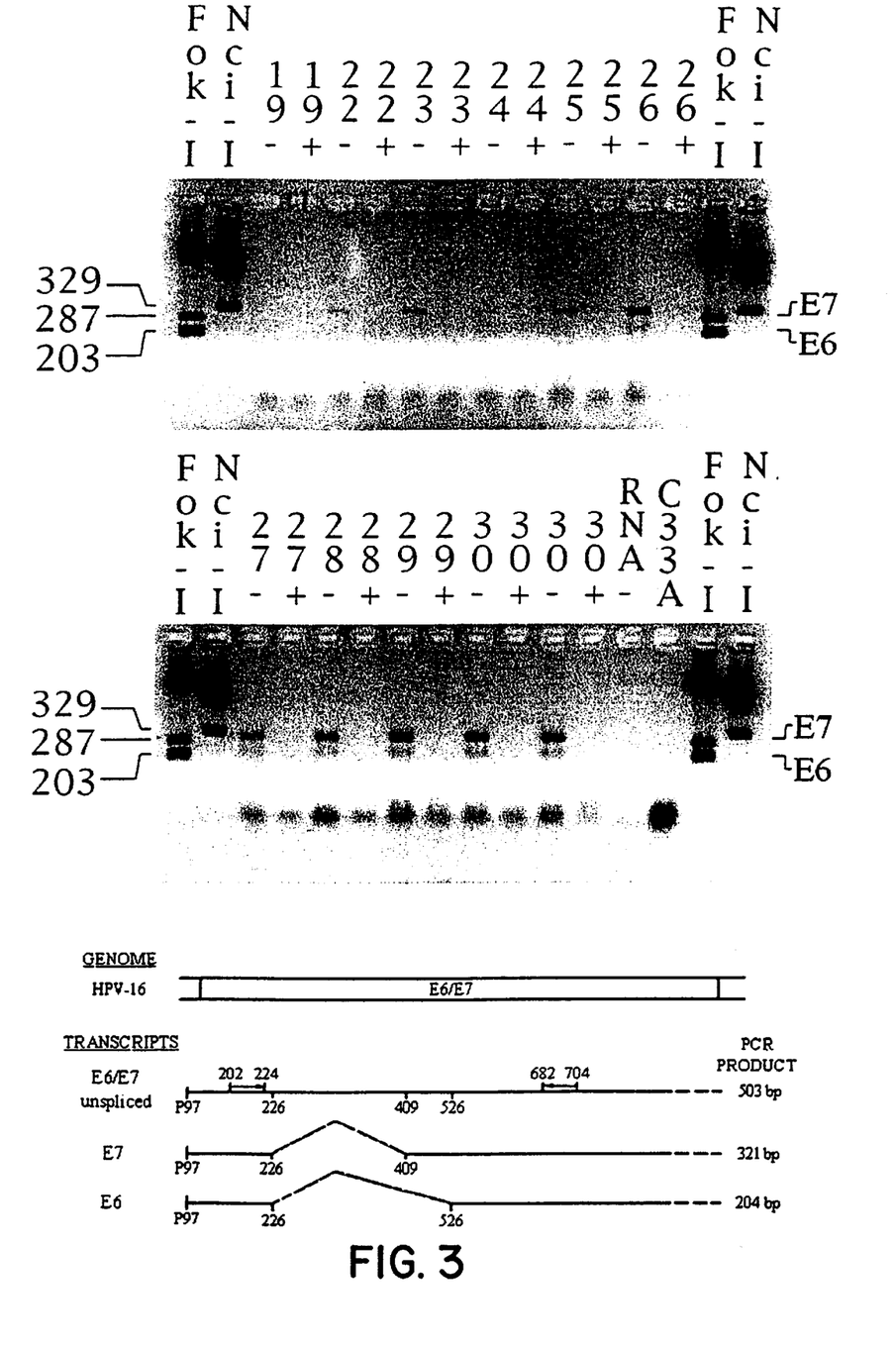

Inhibition of $E_6/E_7$ mRNA synthesis following $M_4N$ treatment was measured by RT-PCR in cervical cell line $C_3$. Relative RT-PCR was performed with quantities of total cellular RNA standardized to the cell numbers counted. The RT-PCR product was analyzed on a 2% agarose gel. The results are shown in FIG. 3. The RT-PCR results indicated that the amplified cDNAs of the expected size for E7 (321 bp) and E6 (204 bp) were detected in the DMSO treated cells as early as cycle 22 of amplification. These same products were barely detectable in the drug treated RNA extracts following 30 cycles of amplification. No amplified products were detected for the no template PCR control or from total RNA extracts of the HPV16-negative C33a cell line.

EXAMPLE 3

Inhibition of Cervical C3 Cell Growth by $M_4N$ Treatment

Figure 4A:
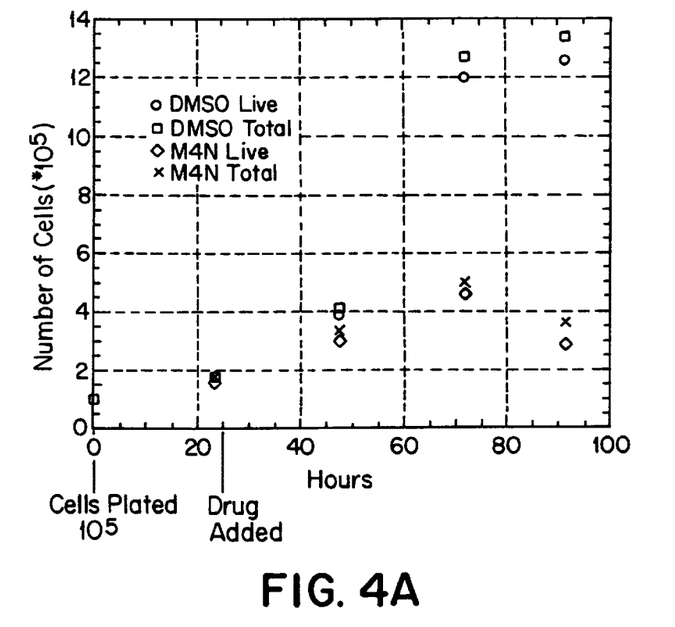
FIG. 4A. Inhibition of C3 Cell Growth by $M_4N$

HPV-16 transformed immortal mouse epithelial cells (C3 cells) were plated at a density of $10^5$ cells per vial. After 24 hours, ½ of the vials were given growth media containing 40 $\mu M M_4N$ dissolved in 1% DMSO while the other half were given growth media containing only 1% DMSO. The results are shown in FIG. 4A. Within 24 hrs a difference in cell morphology between drug treated and control C3 cells was observed. The growth and division of the drug treated cells was markedly reduced in comparison to the untreated control, while the fraction of viable cells compared to the total cell count remained constant for both drug treated and DMSO only control cells. This indicates that $M_4N$ dramatically reduces cell division.

Figure 4B:
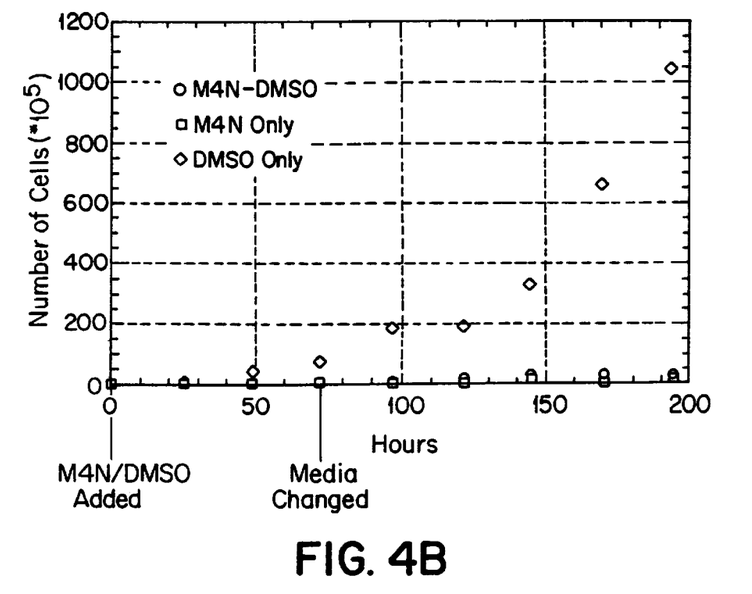
FIG. 4B. Inhibition of C3 Cell Growth Following the Removal of $M_4N$

The effect on C3 growth following removal of $M_4N$ from the medium was also examined. C3 cells were plated at a density of $10^4$ cells per vial. At time=0, ⅔ of the vials were given growth media supplemented with 40 $\mu M$ $M_4N$ in 1% DMSO. The remaining vials were given growth media containing only 1% DMSO. After 73 hours, ½ of the vials that had received $M_4N$ in their growth media were washed and media containing only 1% DMSO was added. The other ⅔ of the cell vials were washed and replaced with the same media administered before. The results, shown in FIG. 4B, indicate that the rate of cell growth was not notably increased in $M_4N$ treated sample following the change to drug-free media, indicating that $M_4N$ continues to significantly reduce cell division even after its removal from the extracellular environment.

EXAMPLE 4

Analysis of Cellular Gene Expression in C3 Cells Before and After 72 Hrs of Drug Treatment Gene expression with 9600 gene arrays was studied (FIG. 5). Five micrograms each of poly $A^+$ RNA from 72 hrs. $M_4N$ (40 $\mu m$) treated ($C_3$ $M_4N$) and non-treated ($C_3$ DMSO) was used in a pair of human 9600 gene array hybridization study according to the procedure described in Genomics 51, 313–324 1998. The hybridization image was captured by a color video camera with a Nikon 55 mm AF micro Niko lens and digitized by a Macintosh LC630 computer. Such detection via enzyme substrate reaction of color-forming enzymes in either single or dual-color mode is reproducible and extremely sensitive (can detect <5 copies of transcript per cell with RNAs from $10^7$ cells).

The computer print outs showing differentially expressed genes ($C_3$ $M_4N/C_3$ DMSO>10 and $C_3$ DMSO/$C_3$ $M_4N$>10) were listed for examination. Image files in TIFF format and data files in MS excel format are kept on ZIP diskette. Gene names and clone ID numbers are available for obtaining Image clones for future northern blot confirmation.

Among a group of genes that are either up-regulated or down-regulated 72 hrs after $M_4N$ treatment, the following are those specifically related to cell division and apoptosis. The following cell cycle related genes are greatly unregulated in response to $M_4N$:

|  | Increase |
|---|---|
| Cyclin-dependent kinase inhibitor | (100X) |
| Apoptosis (APO-1) antigen | (100X) |
| Death Domain Three $DR_3$ | (100X) |
| Ras-related protein RAP-1 | (60X) |
| Human Map Kinase | (40X) |

The following cell cycle related genes are greatly down-regulated in response to $M_4N$:

|  | Treated | Untreated |
|---|---|---|
| Cyclin-dependent kinase 7 | (5%) | 100% |
| Human cytokine receptor | (2%) | 100% |
| Proliferating cell nuclear antigen, PCNA | (1%) | 100% |
| Human TNF-related Apoptosis $APO_2$ | (3%) | 100% |
| Cysteine protease | (7%) | 100% |

At earlier time points, such as after one hour drug treatment, $E_6/E_7$ level was found to be similar with those in control cells while after 4.5 hrs, $E_6/E_7$ were no longer detectable by RT-PCR (39). Gene expressions with 9600 gene arrays can be repeated with RNA isolated from these short-time treated cells (1 hour and 5 hours) in order to further pin down the initial cellular effects of the drug.

EXAMPLE 5

Targeting C3 Tumor Growth in Mice by Local Injection of $M_4N$

Figure 6:
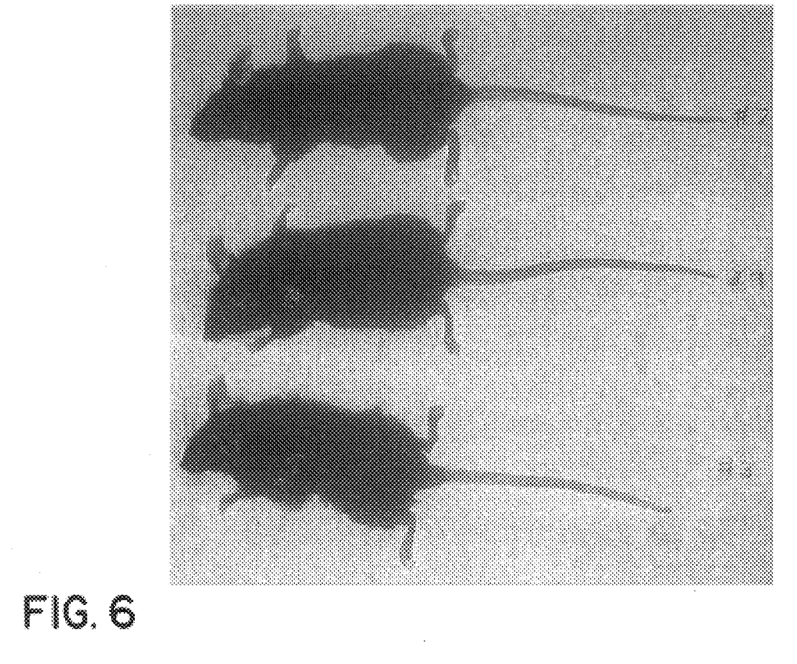
FIGS. 6A–6B. Visual observations of tumor-bearing mice following $M_4N$ treatment. 6A. Mouse bearing single tumor was treated with in situ injection of DMSO (#3) or $M_4N$ (#7). In situ injection of $M_4N$ was also made to one of the two tumors grown in mouse #9. 6B. $M_4N$ treated tumor (white scar) with untreated tumor from the same mouse, #9 as described in Table 2.

Thirty six C57bl-16 NCR mice were injected with $5 \times 10^5$ C3 cells between the shoulders on the backs of the mice. Twenty four of the mice developed tumors within 20 days. They were used for the first set of experiments. Daily injection (50 $\mu l$–100 $\mu l$ of $M_4N$ or $M_4N/G_4N$) (200 mg/ml $M_4N$ in DMSO, 200 mg/ml $G_4N$ in PBS) showed profound effect in tumor growth in animals, as shown in Tables 1 and 2, FIGS. 6 and 7.

TABLE 1

$M_4N$ and $G_4N$ Effect on Growth of Single Tumors Developed in Mice

| Mouse # | Treatment Period | | Lesion Size (mm) | | | Wt. Of Excised Lesion (g) | | Body wt. (g) | | |
|---|---|---|---|---|---|---|---|---|---|---|
| | | | Day 1 | Day 7 | Day 21 | Day 16 | Day 24 | Day 1 | Day 16 | Day 24 |
| | Days 1–16 | | | | | | | | | |
| 1 | DMSO* | | 3 × 8 × 3.3 | — | 5 × 7 × 4 | — | 0.3 | 18.8 | — | 20.2 |
| 2 | DMSO | | 4.4 × 6 × 3.5 | 10 × 12 × 8 | — | 1.56 | — | 19.6 | 20.5 | — |
| 3 | DMSO | | 0.8 × 0.8 × 1 | — | 10.5 × 11 × 9 | — | 1.14 | 18.2 | — | 16.1 |
| 4 | DMSO | | 2.8 × 3.8 × 2.5 | — | 18 × 11 × 9 | — | 2.9 | 17.6 | — | 20.2 |
| 6 | $M_4N$ | | — | 9 × 8 × 5 | — | 0.2 | — | 19 | 19.2 | — |
| 7 | $M_4N$ | | — | 6 × 7 × 7 | — | — | 0.1 | 18.2 | — | 20.4 |
| 11 | $M_4N$ | | 1 × 1.3 × 1 | 9.5 × 10 × 9 | — | — | 0 | 19.5 | — | 20.2 |
| 14 | $M_4N$ | | 3.8 × 3.8 × 3.5 | 8 × 9 × 6 | — | 0.4 | — | 17 | 17.6 | — |
| 15 | $M_4N$ | | — | 5 × 4 × 4 | — | 0.1 | — | 18.9 | 20.0 | — |
| 16 | $M_4N$ | | 2.8 × 2.8 × 2.8 | 9 × 6 × 4 | — | 0 | — | 17.2 | 17.6 | — |
| 17 | $M_4N$ | | 2.3 × 2.3 × 2.3 | 6 × 6 × 4 | — | 0.2** | — | 17.3 | — | — |
| | Days 1–10 | Days 9–17 | | | | | | | | |
| 18 | $M_4N$ | $G_4N$ | 3 × 2.8 × 3 | 8 × 7 × 5 | — | — | 1.0*** | 18.8 | — | 21.1 |
| 19 | $M_4N$ | $G_4N$ | — | 5 × 5 × 5 | — | 0.2 | — | 18.2 | 19.9 | — |
| 21 | $M_4N$ | $G_4N$ | 1.8 × 1.8 × 1.8 | 9 × 10 × 5 | — | 0.2 | — | 17.3 | 19.2 | — |
| 22 | $M_4N$ | $G_4N$ | — | 7 × 7 × 5 | — | — | 0 | 17.9 | — | 19.5 |
| 27 | $M_4N$ | $G_4N$ | 2.5 × 5 × 2.5 | 9 × 6 × 6 | — | — | 1.8*** | 20 | — | 20.7 |
| 28 | $M_4N$ | $G_4N$ | 2.8 × 2.3 × 2.8 | 5 × 5 × 4 | — | 0.17 | — | 18.1 | 19.8 | — |
| 29 | $M_4N$ | $G_4N$ | 2.8 × 2.5 × 2.8 | 5 × 6 × 4 | — | — | 0.2 | 18.8 | — | 19.6 |

Figure 7:
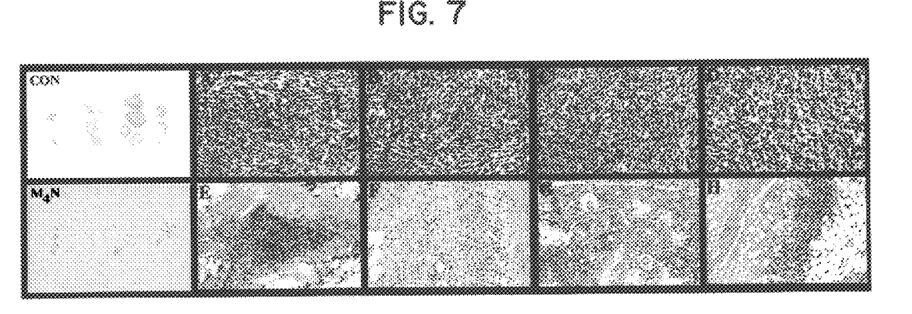
FIG. 7. Effect of $M_4N$ and $M_4N/G_4N$ on Tumor Growth in Mice

*DMSO = Vehicle for Drug
**Taken on Day 15
***Lesion contained mostly necrotic cells as also found in lesions from mouse 6, 7, 11, 14, 15, 17, 19, 21, 28, 19 (FIG. 6, 7). There were no lesions left in mouse #11 and #22 following drug treatments. Tumors found in control mouse #1, 2, 3, 4 contained growing cells (FIG. 2).

Experimental Procedures

36 C57bl-16NCR mice were injected with 5×10⁵ C3 cells/mouse. Injections were 100 μL made subcutaneously between the shoulders on the backs of the mice. Cells were suspended in low-salt HBSS and suspension uniformity was maintained by gentle vortexing.

24 mice developed tumors. Their lesion sizes were measured by dial caliper. These mice were shaved, weight and treatment begun (Day 1). Four mice were sequestered as controls. Control mice received 50 μL DMSO injected intratumorally daily. Experimental mice (10) received 50 μL $M_4N$ dissolved in DMSO (200 mg/mL). An additional 10 mice received $M_4N$ treatments for 8 days followed by $G_4N$ treatments (50 μL, 200 mg/mL in PBS) daily for 8 days. Injections were made to several regions of tumor. Mice anesthetized with ether or metaphane prior to injection.

TABLE 2

$M_4N$ and $G_4N$ Effect on Growth of Treated Lesions in Mice Carrying Multiple Tumors

| Mouse # | Treatment Period | | Lesion Size (mm) | | Wt. Of Excised Lesion (g) | | Body wt. (g) | |
|---|---|---|---|---|---|---|---|---|
| | | | Day 1 | Day 7 | Treated* | Not Treated** | Day 1 | Day 24 |
| | Days 1–16 | | | | | | | |
| 9 | $M_4N$ | | 1.3 × 5 × 0.75 | 7 × 9 × 8 | 0.25 | 0.6 | 20.2 | 17.9 |
| 10 | $M_4N$ | | 2.3 × 2.5 × 2.3 | 9.5 × 10 × 9 | 0.1 | 2.9 | 17.5 | 22.1 |
| 12 | $M_4N$ | | 2.5 × 2.5 × 2.5 | 8 × 9 × 6 | 0.11 | 1.82 | 17.8 | 20.0 |
| | Days 1–9 | Days 10–18 | | | | | | |
| 20 | $M_4N$ | $G_4N$ | 1.8 × 1.8 × 1.8 | 9 × 10 × 5 | 0.1 | 0.2 | 17 | 20.2 |
| 24 | $M_4N$ | $G_4N$ | — | 7 × 9 × 6 | 0 | 1.7 | 17.2 | 20.8 |
| 26 | $M_4N$ | $G_4N$ | 5 × 3.3 × 2.5 | 7 × 7 × 7 | 0.2 | 1.9 | 19.3 | 20.6 |

*Drug in DMSO was injected directly to the tumor regions
**From adjacent tumors deprived of drug

TABLE 3

Toxicity Studies of $G_4N$ in Mice

| Group | | # of Mice | Route | Treatment per day | Days of Injection | Mortality |
|---|---|---|---|---|---|---|
| 1 | 187.5 mg/kg | 3 | Subcutaneous | 2× | 6 | 0/3 |
| 2 | 375 mg/kg | 3 | Subcutaneous | 1× | 6 | 0/3 |

TABLE 3-continued

Toxicity Studies of $G_4N$ in Mice

| | Group | # of Mice | Route | Treatment per day | Days of Injection | Mortality |
|---|---|---|---|---|---|---|
| 3 | 750 mg/kg | 4 | Subcutaneous | 1× | 6 | 1/4 |
| 4 | 375 mg/kg | 2 | IV | 2× | 6 | 0/2 |

C57BL-16NCR female mice from NCl were used in this experiment. Tetraglycinal NDGA ($G_4N$) was freshly made everyday in PBS in concentrations of 75 mg/ml. Injections of 0.05 ml for group 1, 0.1 ml for groups 2 and 4, and 0.2 ml for group 3 per treatment were made for a period of 6 days. Experiments lasted seven days. Body weights were determined before and after six days of injection. No significant weight changes were observed during the experimental period.

All treated mice, controls (mouse numbers 1–4) and experimental mice (mouse numbers 6,7,9,10,11,12,14,15, 16,17 $M_4N$ numbers 18–22, 24, 26–29 $M_4N/G_4N$) exhibited swelling. Measurements of lesion sizes were made by dial caliper. Some mice experienced mild bleeding due to injection. The treatment regimen and results were as follows:

Day 10: Mice weighed again. All mice exhibited growth up to two grams.
Day 12: No treatments made.
Day 13: All mice have raised skin but to very different degrees. The skin of one $M_4N$ treated mouse (#7) has split open through which the "dried-out tumor" fell out.
Day 14: Injection volume raised to 100 µL.
Day 15: One $M_4N$ treated mouse (#17) died due to overdose of anesthesia/handling. The skin at the lesion site of #17 cracked with the "dried-out tumor" showing. It was dissected, and lesion excised and weighed.
Day 16: Four more $M_4N$ treated mice (#6,14,15,16), three $M_4N/G_4N$ treated mice (#19,21,28) and one control mouse (#2) were euthanized, dissected and weighed. Remaining control mice (#1,3,4) were examined non-invasively and were carrying tumors.
Day 21: Tumor sizes from control mice were measured by dial caliper. Observation: The skin at the lesion sites of mouse #10 and #12 ($M_4N$ treated regions) cracked with the "dried-out tumor" showing.
Day 24: Mouse #7 skin recovered completely. The experiment was terminated on this date. All remaining mice, $M_4N$ treated (#7,9,10,11,12) and $M_4N/G_4N$ treated (#18, 20,24,26,29) were euthanized, dissected, examined and weighed.

The effects of $M_4N$ and $M_4N/G_4N$ on C3 tumor growth in mice are summarized in Tables 1 and 2 and FIGS. 5 and 6. Table 1 shows the drug effect on C3 cell growth in mice carrying single tumors. The average weight of four excised tumors of the control group was 1.48 g while weights of lesions from $M_4N$ treated and $M_4N/G_4N$ treated were 0.142 and 0.51 g respectively. Drug treated lesions consisted mainly of dried out necrotic cells (FIG. 6). Tumors from the control group appeared homogenous and contained actively growing cells. Table 2 shows the drug effect on C3 tumor growth in mice carrying multiple tumors. In this study, drug was injected into one of the tumors. The average weight of untreated tumors was 1.77 g while that of $M_4N$ treated lesions was 0.15 g. Similar results were obtained following $M_4N/G_4N$ injection—the average weight of untreated tumors was 1.27 g, while that of the drug treated lesions was only 0.103 g.

The body weight changes of all mice during the entire experimental period appeared insignificant (Table 1 and 2).

EXAMPLE 6

Drug treated ($M_4N$) and DMSO vehicle-treated or untreated tumors (CON) from two groups of mice were prepared for histopathology examination. The excised tumors were immediately fixed and then stored in 4% formaldehyde in phosphate buffered saline. The fixed tissue was then dehydrated through a series of graded alcohols and xylene and embedded in paraffin. The paraffin tissue blocks were thin sectioned and stained for microscopy with hematoxylin and eosin. Histopathology studies showed that the control tumors were unaffected by DMSO treatment and continued to grow. They show the high nuclear/cytoplasmic ratio, pleomorphic nuclear changes, high mitotic figures, spindle like sarcoma shape, and infiltration into the surrounding tissue characteristic of cancer cells.

In contrast, those tumors receiving $M_4N$ treatment discontinued growth shortly after treatment began. They demonstrate significant necrosis and are no longer viable. There is a small amount of drug precipitate visible at higher magnification, and focal areas show chronic inflammation and fibrosis. This healing effect leads to the shedding of these deceased tumor cells from the area. The same results are seen with $M_4N/G_4N$ treatment as with the $M_4N$ treatment alone. However, since $G_4N$ is water-soluble, it can spread to a larger area of the tumor than $M_4N$. $G_4N$ when used with $M_4N$ synergistically is more effective in trating tumors of larger than 2 $cm^3$.

EXAMPLE 7

Effect of $M_4N$ on HSV-1 Skin Infection in Guinea Pig

The drug $M_4N$ was also tested in inhibition of HSV-1 replication in skin infections in guinea pigs. Guinea pig skin was pinched with needles and HSV-1 suppression was applied topically to infect each pricked area. $M_4N$ was then applied to the pricked infected area following infection daily for 6 days.

Figure 8:
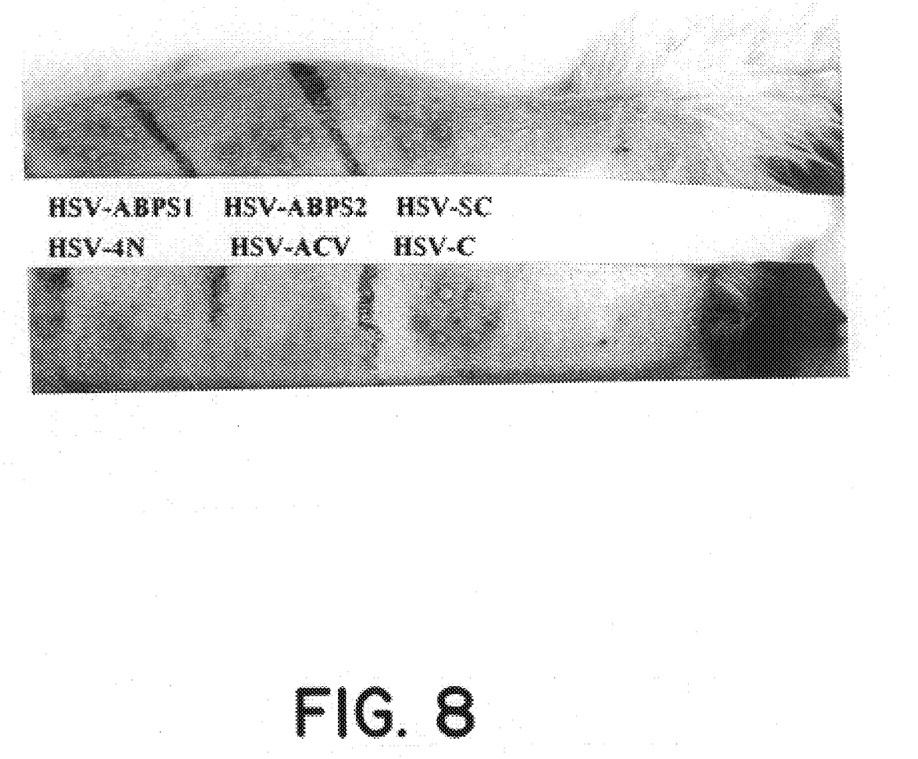
FIG. 8. HSV-1 replication in the absence of drugs (HSV-C, HSV-SC), in the presence of ineffective drugs (ABDS$_1$ ["HSV-ABDS$_1$"], ABDS$_2$ ["HSV-ABDS$_2$"]) and in the presence of effective drugs ($M_4N$ ["HSV-4N"] and ACV ["HSV-ACV"]).

Six areas of bared back skin of a guinea pig were punched sterilely with a 5=DIN needle. Two areas were infected with HSV-1 (HSV-C, culture supernatant, or isolated HSV in saline, HSV-SC). The other four areas were infected with HSV-SC. Fifteen minutes after infection, 30 µl of test compounds ($ABDS_1$, $ABDS_2$, ACV and $M_4N$ (4N) in 60 mg/ml of DMSO were applied to each punched infected region of an area, five times per day for six days. $ABDS_1$ and $ABDS_2$ were included as negative controls. The photograph in FIG. 8 was taken at day 6 and shows the extent of HSV-1 replication in the absence of drugs (HSV-C, HSV-SC), in the presence of ineffective drugs (HSV-$ABDS_1$, HSV-$ABDS_2$) and in the presence of effective drugs (HSV-$M_4N$ and HSV-ACV). It can be seen that six large confluent blisters were developed in areas treated by HSV-C, HSV-SC, HSV-$ABDS_1$, HSV-$ABDS_2$, while no blisters were observed in infected areas following $M_4N$ (4N) and ACV treatments.

Clearcut results that $M_4N$ can block HSV replication were obtained in this model system as shown by the disappearance of the skin lesions and by no shedding of the virus 4 days after the drug treatment. Initial animal studies also showed $M_4N$ to be non-toxic to mice at concentrations as high as 300 mg/kg when given intraperitoneally, and as high as 375 mg/kg when given either subcutaneously or by IV (Table 3) (6).

EXAMPLE 8

$M_4N$ for Clinical Treatment Using in situ Injection

Administration of $M_4N$ directly into tumors as a drug delivery route provides several distinctive advantages. 1)

M₄N is a hydrophobic compound and is exceedingly soluble in DMSO (200 mg/ml). Therefore only a small volume of the drug solution is needed for injection in order to achieve effective dosage of the drug. In the mouse study described in Example 5, above, daily injection of 50 µl to 100 µl for several days was sufficient to completely stop tumor growth in mice. There have been several previous studies on the use of large dosages (30 ml IV per treatment) of DMSO for treating diseases (14). The results were not conclusive (15). However, since tens of millions of people have been safely tested with large amounts of DMSO worldwide in the past, it appears that DMSO should be safe as a vehicle for drug delivery when only small volume of it will be used (16). 2) By injection in situ, a majority of the drug residue remains insoluble and concentrated in the tumor areas, and does not enter the circulatory system, thus whole body toxicity is avoided. In addition, since enough drug remains within the tumor to suppress its growth, continued injection of drug is unnecessary after relatively few treatments. In the mouse study of Example 5, tumor cells continued to die even after discontinuation of M₄N injections. Thus when drug is directly targeted, tumor size becomes the determining factor for the required amount of drug to be administered. The difference between whole body weights of a human vs. a mouse becomes irrelevant. In the mouse tumor studies, 20 mg/day for 10 days were more than sufficient to eliminate tumors. There should be no reason to use a higher dosage than this for treating a human tumor of comparable size (1–1.5 cm³). This should reduce the risk considerably in human trials.

References cited herein are listed below for convenience and are hereby incorporated by reference.

1. Baba, M. (1997) Mini Review. Cellular Factors as Alternative Targets for inhibition of HIV-1. *Antiviral Res.* 33, 144 i–1452.
2. Gnabre, J. N., Brady, J. N., Clanton, D. J., Ito, Y., Dittmer, J., Bates, R. B. and Huang, R. C. (1995) Inhibition of Human Immunodeficiency Virus Type 1 Transcription and Replication by DNA Sequence-Selected Plant Lignans. *Proc. Natl. Acad. Sci.* U.S.A. 92, 11239.
3. Gnabre, J. N., Ito, Y., Ma. Y. and Huang, R. C. (1996) Isolation of Anti-HIV-1 Lignans from *Larrea Tridentata* by Counter-Current Chromatography. *J. Chromatogr.* A 719, 353.
4. Gnabre, J. N., Huang, R. C., Bates, R. B., Burns, J. J., Calder, S., Malcomson, M. E. and McClure, K. J. (1995) Characterization of Anti-HIV Lignans from *Larrea Tridentata Tetrahedron* 51, 12203.
5. Hwu, J. R., Tseng, W. N., Gnabre, J., Giza, P. and Huang, R. C. C. (1998) Antiviral Activities of Methylated Nordihydroguaiaretic Acids (I) Synthesis, Structure Identification and Inhibition of Tat Regulated HIV Transactivation. *J. Med. Chem.* 41:2994–3000.
6. Chen, H., Teng, L., Li, J.-N., Park, R., Mold, D. E., Gnabre, J., Hwu, J. R., Tseng, W. N. and Huang, R. C. C. (1998) Antiviral Activities of Methylated Nordihydroguaiaretic Acids (II) Targeting Herpes Simplex Virus replication by the Mutation Insensitive Transcription Inhibitor Tetra-O-methyl-NDGA. *J. Med. Chem.* 41:3001–3007.
7. Honess, R. W., and Roizman, B. (1988) Regulation fo Herpes Virus Macromolecular Synthesis. 1. Cascade Regulation of Synthesis of Three Groups of Viral Proteins. J. Virol. 1974. 14, 8.
8. Courey, A. J., and Tjian. R. (1988) Analysis of Sp1 in vivo Reveals Multiple Transcription Domains. Including a Novel Glutamine-rich Activation Motif. *Cell* 55, 887.
9. Some of the Sp1-regulated cellular genes: Sartorelli, V.; Webster, K. A.; Kedes, L. Muscle-specif~c expresison of the cardiac alpha-actin gene requires myoD1, CarG-hox binding factor and Sp1. *Gene Dev.* 1990, 4, 1811. Dailey, L.; Roberts, S. B.; Heintz, N. Purification of the histone H4 gene-specific transcription factors, H4TF-1 and H4TF-2. *Gene Dev.* 1988, 2, 1700. Means, A. L.; Farnham, P. J. Transcription initiation form the dihydrogolate reductase promoter is positioned by HIP-I binding at the initiation site. *Mol Cell Biol.* 1990, 10, 653. Abravaya, K.; Phillips, B.; Morimoto, R. I. Heat shock-induced interaction so heat shock transcription factor and human hsp70 promoter examined by in vivo footprinting. *Mol. Cell Biol.* 1991, 11, 586. Leask, A.; Rosenberg, M.; Vassar, R.; Fuchs, E. Regulation fo a human epidermal keratin gene: Sequences and nuclear factors involve din keratinocyte-specific transcription. *Gene Dev.* 1990, 4, 1985. Desjardins, E.; Hay, N. Repeated CT elements bound by zinc finger proteins control the absolute and relative activities of the two principal huyman cmyc promoter. *Mol. Cell Biol.* 1993, 13, 5710. Sanchez, H. B.; Yieh, L.; Osborne, T. F. Cooperation by sterol regulatory element-binding proteins and Sp1 in sterol regulation of low-density lipoprotein receptor gene. *J. Biol Chem.* 1995, 270, 1161. Lemaigre, F. P.; Lafontaine, D. A.; Courtois, S. J.; Durviaux, S. M.; Rousseau, G. G. Sp1 can displace GHF-1 from its distal binding site and stimulate transcription form growth hormone gene promoter. *Mol.l Cell. Biol.* 1990, 10, 1811.
10. Phelps, W. C., Yee, C. L., Munger, K. and Howley, P. M. (1988) The Human Papilloma Virus Type 16 E7 Gene Encodes Transactivation and Transformation Functions Similar to Those of Adenovirus E/A. *Cell* 53, 539–547.
11. Greenstone, H. L. Nieland, J. D., DeVisser, K. E., DeBruijn, M. L., Kimbauer, R., Roden, R. B., Lowy, D. R., Kast, W. M. and Schiller, J. T. (1998) Chimeric Papillomavirus Virus-Like particles Elicit Antitumor Immunity Against the E₇ Oncoprotein in an HPV16 Tumor Model. *PNAS* 95,1800–1805.
12. Feltkamp, M. C., Vreugdenhil, G. R., Vierboom, M. P., Ras, E., Van der Burg, S. H., Schegget, J. Ter, Melief, C. J. M. and Kast, W. M. (1995) CTL Raised Against a Subdominant Epitope Offered as a Synthetic Peptide Eradicate Human Papillonavirus Type 16-Induced Tumors. *European Journal of Immunology* 25, 2638–2642.
13. Feltkamp, M. C., Smits, H. L., Vierboom, M. P., Minaar, R. P., B. M. Drijfhout, J. W., Schegget, J., Melief, C. and Kast, W. M. (1993) Vaccination with Cytotoxic T Lymphocyte Epitope-Containing Peptide Protects Against a Tumor Induced by Human Papillomavirus Type 16-Transformed Cells. *Eur. J Immunol.* 23, 2242–2249.
14. Jacob, S. W. and Herschler (1986) Pharmacology of DMSO. *Academic Press, Inc.*
15. Jack, C., and Torre, de la (1983) Biological Actions and Medical Applications of Dimethyl Sulfoxide. New York Academy of Sciences, New York, N.Y.
16. Spruance, S. L., McKeough. M. B. and Cardinal, J. R. (1983) Dimethyl Sulfoxide as a vehicle for topical antiviral chemotherapy. *Ann. N. Y. Acad. Sci.* 411, 28–33.

What is claimed is:

1. A method for treating an HPV-induced tumor, said method comprising application of at least one nordihydroguiaretic acid derivative of the formula wherein $R_1$, $R_2$, $R_3$ and $R_4$ independently represent —OH, —OCH$_3$, —O(C=O)CH$_3$, or an amino acid residue, but are not each —OH simultaneously, to said tumor.

2. The method of claim 1 wherein said tumor is present in a mammal.

3. The method of claim 2 wherein said mammal is a human.

4. The method of claim 1 wherein said tumor is cervical or oral cancer.

5. The method of claim 1 wherein said tumor is derived from transformed cells.

6. The method of claim 5 wherein said cells are $C_3$ cells.

7. The method of claim 1 wherein said tetramethyl nordihydroguiaretic acid is administered along with at least one pharmaceutically acceptable excipient or carrier.

8. The method of claim 7 wherein said excipient or carrier is dimethylsulfoxide (DMSO).

9. A pharmaceutical composition comprising tetraglycinylnordihydroguiaretic acid along with at least one pharmaceutically acceptable excipient or carrier.

10. The composition of claim 9 wherein said excipient or carrier is physiological saline.

11. Tetraglycinylnordihydroguiaretic acid.

12. A method for treating an HPV-induced tumor, said method comprising application of tetraglycinyl nordihydroguiaretic acid to said tumor.

13. The method of claim 12, wherein tetraglycinyl nordihydroguiaretic acid is applied topically.

14. The method of claim 12, wherein tetraglycinyl nordihydroguiaretic acid is applied by injection into said tumor.

15. The method of claim 12 which additionally comprises the application of tetramethyl nordihydroguiaretic acid to said tumor.

* * * * *